United States Patent
Don et al.

(10) Patent No.: US 10,456,102 B2
(45) Date of Patent: Oct. 29, 2019

(54) AUTOMATED APPARATUS TO IMPROVE IMAGE QUALITY IN X-RAY AND ASSOCIATED METHOD OF USE

(71) Applicants: WASHINGTON UNIVERSITY, St. Louis, MO (US); CHILDREN'S MEDICAL CENTER CORPORATION, Boston, MA (US)

(72) Inventors: Steven Don, St. Louis, MO (US); Robert MacDougall, Cambridge, MA (US); William Clayton, O'Fallon, IL (US)

(73) Assignees: WASHINGTON UNIVERSITY, St. Louis, MO (US); CHILDREN'S MEDICAL CENTER CORPORATION, Boston, MA (US)

( * ) Notice: Subject to any disclaimer, the term of this patent is extended or adjusted under 35 U.S.C. 154(b) by 702 days.

(21) Appl. No.: 15/100,022

(22) PCT Filed: Nov. 26, 2014

(86) PCT No.: PCT/US2014/067765
§ 371 (c)(1),
(2) Date: May 27, 2016

(87) PCT Pub. No.: WO2015/081295
PCT Pub. Date: Jun. 4, 2015

(65) Prior Publication Data
US 2017/0007196 A1 Jan. 12, 2017

Related U.S. Application Data

(60) Provisional application No. 61/909,438, filed on Nov. 27, 2013.

(51) Int. Cl.
*A61B 6/00* (2006.01)
*A61B 6/03* (2006.01)
(Continued)

(52) U.S. Cl.
CPC .............. *A61B 6/544* (2013.01); *A61B 6/032* (2013.01); *A61B 6/4417* (2013.01); *A61B 6/461* (2013.01);
(Continued)

(58) Field of Classification Search
CPC ....... A61B 6/032; A61B 6/4417; A61B 6/461; A61B 6/505; A61B 6/5264; A61B 6/544;
(Continued)

(56) References Cited

U.S. PATENT DOCUMENTS 6,954,513 B2    10/2005   Horiuchi
7,469,035 B2    12/2008   Keall et al.
(Continued)

FOREIGN PATENT DOCUMENTS

DE    19/802499 A1    7/1999
EP    0346530 A1    12/1989
(Continued)

OTHER PUBLICATIONS

Extended European Search Report for EP 14866125.9 dated Jul. 3, 2017.
(Continued)

*Primary Examiner* — Chih-Cheng Kao
(74) *Attorney, Agent, or Firm* — Thompson Coburn LLP

(57) ABSTRACT

A system or method for improving quality in projection and tomographic x-ray, which includes a depth sensing device to measure a depth of at least one body part of a patient from the depth sensing device and a control unit to calculate a thickness and/or circumference of the body part using the depth information. The calculated thickness and circumference information is used to determine an optimal level of x-ray exposure for the body part. The system or method also includes a camera to identify the body part that needs to be examined and to detect any motion of the identified body part.

5 Claims, 13 Drawing Sheets

(51) Int. Cl.
*G01B 11/06* (2006.01)
*G01B 11/25* (2006.01)
*G01N 23/046* (2018.01)

(52) U.S. Cl.
CPC ............ *A61B 6/463* (2013.01); *A61B 6/5264* (2013.01); *G01B 11/06* (2013.01); *G01B 11/25* (2013.01); *G01N 23/046* (2013.01); *A61B 6/505* (2013.01)

(58) Field of Classification Search
CPC ........ A61B 6/463; G01B 11/06; G01B 11/14; G01B 11/22; G01B 11/25; G01N 23/046
See application file for complete search history.

(56) References Cited

U.S. PATENT DOCUMENTS

| | | |
|---|---|---|
| 8,538,776 B2 | 9/2013 | Reiner |
| 2001/0012330 A1 | 8/2001 | Ogura et al. |
| 2005/0013410 A1 | 1/2005 | Hornegger |
| 2006/0056680 A1 | 3/2006 | Stutsman et al. |
| 2008/0166033 A1 | 7/2008 | Bueno et al. |
| 2011/0060247 A1 | 3/2011 | Payne et al. |
| 2012/0027174 A1 | 2/2012 | Takamura |
| 2012/0165652 A1 | 6/2012 | Dempsey |
| 2016/0213329 A1* | 7/2016 | Dirkes ................. A61B 6/4452 |

FOREIGN PATENT DOCUMENTS

| | | |
|---|---|---|
| JP | 2013233420 A | 11/2013 |
| WO | 2013072872 A1 | 5/2013 |
| WO | 2015/081295 A1 | 6/2015 |

OTHER PUBLICATIONS

Johnson et al., "Skin Dose Mapping for Fluoroscopically Guided Interventions", Medical Physics, Oct. 2011, p. 4 Lines 2-4, vol. 38 No. 10.

International Search Report and Written Opinion for PCT/US2014/067765 dated Apr. 29, 2015.

International Preliminary Report on Patentability (Chapter I) for PCT/US2014/067765 dated May 31, 2016.

* cited by examiner

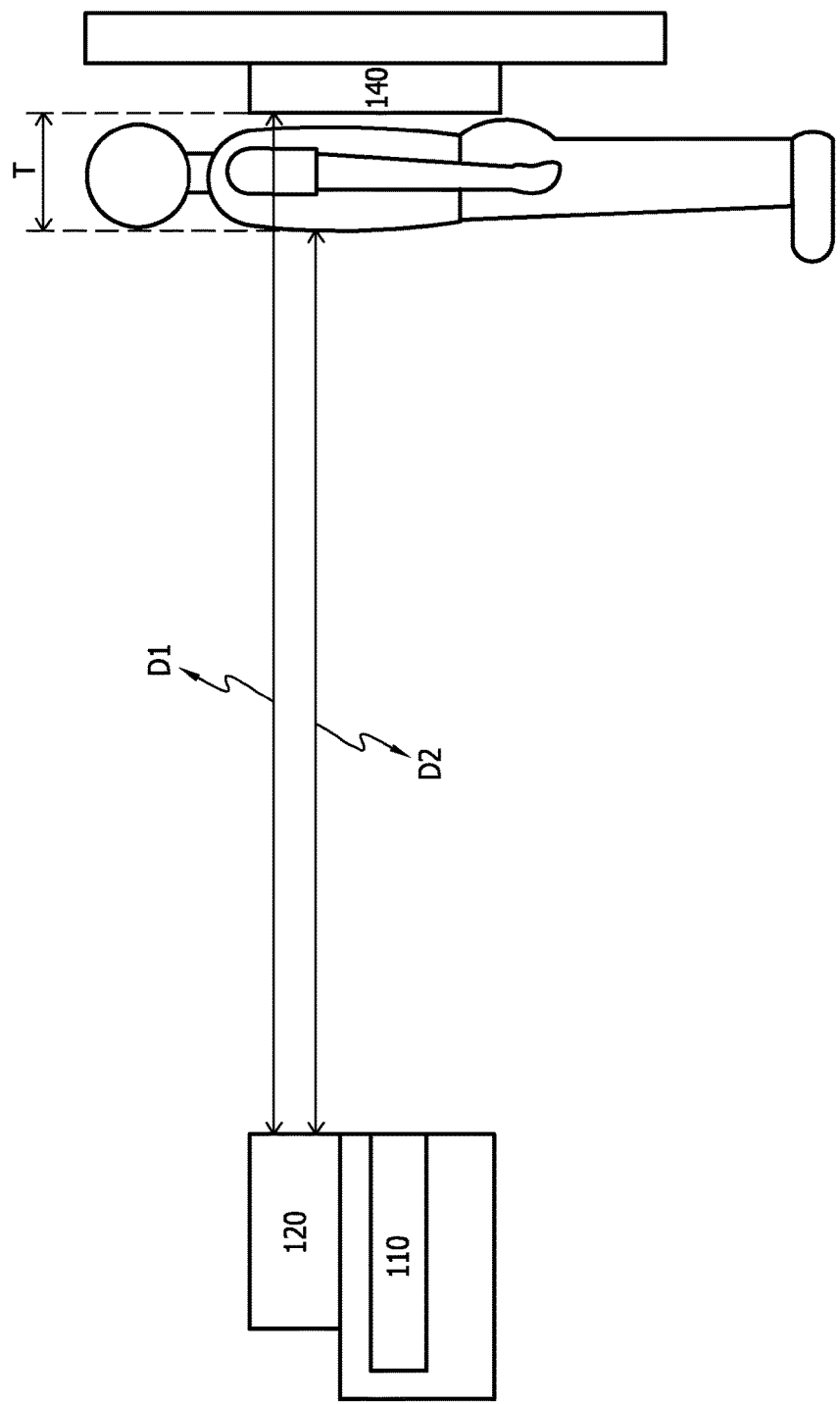

| Header | | |
|---|---|---|
| Unknown | 0011,107e | (Patient Thickness) 8 — 610 |
| Unknown | 0011,1180 | (Motion Index) 0.4 |
| Unknown | 0011,1081 | AP |
| Unknown | 0011,1082 | GRID_FREQ_70_LP_CM |
| BodyPartExamined | 0018,0015 | Left Wrist — 620 |
| KVP | 0018,0060 | 90.000000 |
| SoftwareVersions | 0018,1020 | dm_Platform_release-FW35_4-2012 |
| ProtocolName | 0018,1030 | (CHEST_2_VIEW |
| DistanceSourcetoDetector | 0018,1110 | 101.4 |
| DistanceSourcetoPatient | 0018,1111 | 93.4 |
| FieldViewShape | 0018,1147 | RECTANGLE |
| ▶FieldViewDimensions | 0018,1149 | 148\226 |
| ExposureTime | 0018,1150 | 9 |
| X-rayTubeCurrent | 0018,1151 | 202 |
| Exposure | 0018,1152 | 2 |
| ExposureinuAs | 0018,1153 | 1792 |
| ImageAreaDoseProduct | 0018,115e | 0.1266 — 630 |
| FilterType | 0018,1160 | MULTIPLE |
| ▶ImagerPixelSpacing | 0018,1164 | 0.194225\0.194225 |
| ▶Grid | 0018,1166 | FIXED\FOCUSED |
| FocalSpots | 0018,1190 | 0.6000000 |
| AcquisitionDeviceProcessingDescription | 0018,1400 | antero-posterior^Factory3 |
| RelativeX-rayExposure | 0018,1405 | 50 |
| ExposureIndex | 0018,1411 | 143.24908492874553 |
| TargetExposureIndex | 0018,1412 | 155.40644712976442 |
| DeviationIndex | 0018,1413 | -0.4 |
| PositionerType | 0018,1508 | |
| CollimatorShape | 0018,1700 | POLYGONAL |
| ▶VerticesofthePolygonalCollimator | 0018,1720 | 1441\1541\576\1536\576\486\1441\481 |
| ViewPosition | 0018,5101 | AP |
| EntranceDoseinmGy | 0040,8302 | 0.051 |

FIG. 6

AUTOMATED APPARATUS TO IMPROVE IMAGE QUALITY IN X-RAY AND ASSOCIATED METHOD OF USE

CROSS-REFERENCE TO RELATED APPLICATIONS

This patent application is a U.S. National Phase application of PCT/US 2014/067765, filed on Nov. 26, 2014, claiming the benefit of U.S. Provisional Patent Application Ser. No. 61/909,438, filed on Nov. 27, 2013, and entitled "Automated apparatus to Improve Image Quality in X-ray," both of which are incorporated herein by reference in their entireties.

BACKGROUND OF THE INVENTION

Image quality and patient safety are inextricably linked in medical imaging employing x-rays. Improved image quality leads to improved diagnostic accuracy, which in turn, leads to real patient benefit. However, it is critical not to attempt to achieve the best possible image quality at the expense of increasing patient risk from radiation. At the same time, poor image quality also presents real patient risk when the delivered radiation fails to provide the maximum benefit by yielding accurate diagnosis.

The main determinant of image quality is a radiation dose to an image receptor, as more radiation dose will inherently contain more signal by virtue of x-ray statistics. Minimizing patient dose, however, will degrade the x-ray statistics and degrade image quality. At a certain level of radiation dose, no more relevant information exists in the context of diagnostic accuracy. Thus, the goal of medical staff is to use a technique that provides adequate information consistently without excessive radiation.

A significant problem with current x-ray techniques involves underexposure or overexposure due to a failure to determine the size of the body or body part correctly.

Another problem with current x-ray imaging is that on occasion the wrong body part may be ordered and imaged.

Another set of problems with current x-ray imaging techniques is the detrimental effects caused by patient movement, positioning, and misalignment.

The present invention is directed to overcoming one or more of the problems set forth above.

SUMMARY OF INVENTION

This section provides a general summary of the disclosure and is not a comprehensive disclosure of its full scope or all of its features.

An aspect of this invention provides a system for improving quality in projection and tomographic x-ray imaging comprising: an x-ray tube emitting x-rays; a depth sensing device measuring a depth of at least one body part of a patient, wherein the depth represents a distance between said depth sensing device and the body part; and a control unit comprising a memory, wherein said memory stores depth reference data that represents the distance between said depth sensing device and the body part, wherein said depth reference data is used to calculate one of a thickness of the body part and a circumference of the body part, wherein the calculated thickness or circumference is used to determine an optimal level of x-ray exposure for the body part.

Another aspect of this invention provides a method for improving quality in projection and tomographic x-ray imaging comprising: measuring a depth of at least one body part of a patient with a depth sensing device, wherein the depth represents a distance between said depth sensing device and the body part; storing depth reference data in a memory associated with a control unit, wherein the depth reference data represents the depth of the body part; and calculating one of a thickness of the body part and a circumference of the body part using the depth reference data; and determining an optimal level of x-ray exposure of the body part using one of the thickness of the body part and the circumference of the body part.

Still another aspect of this invention provides a system for improving quality in projection and tomographic x-ray imaging comprising: an x-ray tube; an image receptor; a depth sensing device, wherein said image receptor is positioned to be aligned with said depth sensing device; a RGB camera; and a display device, wherein said display device is configured to display a depth-image view, collimated view, and skeleton view, wherein the depth-image view comprises a plurality of pixels, each of which represents a distance between said depth sensing device and each point of said image receptor that corresponds to each pixel, wherein the distance is measured by said depth sensing device, the collimated view comprises a targeted body part field, and an image receptor field, the skeleton view comprises an overlay of a patient's body, wherein the patient is positioned between said x-ray tube and said image receptor, wherein the patient's body is displayed in a form of skeleton frame comprising a plurality of pre-defined joints of the body, wherein said RGB camera captures a plurality of frames of the patient's body.

These are merely some of the innumerable aspects of the present invention and should not be deemed an all-inclusive listing of the innumerable aspects associated with the present invention. These and other aspects will become apparent to those skilled in the art in light of the following disclosure and accompanying drawings.

BRIEF DESCRIPTION OF DRAWINGS

The drawings described herein are for illustrative purposes only of selected embodiments and not all possible implementations, and are not intended to limit the scope of the present disclosure.

FIG. 2A is a schematic block diagram of an exemplary embodiment measuring a thickness of a patient's body;

FIG. 6 is a drawing of an exemplary embodiment showing the Digital Imaging and Communications in Medicine (DICOM) headers that incorporate the thickness of a patient's body part;

Figure 1:
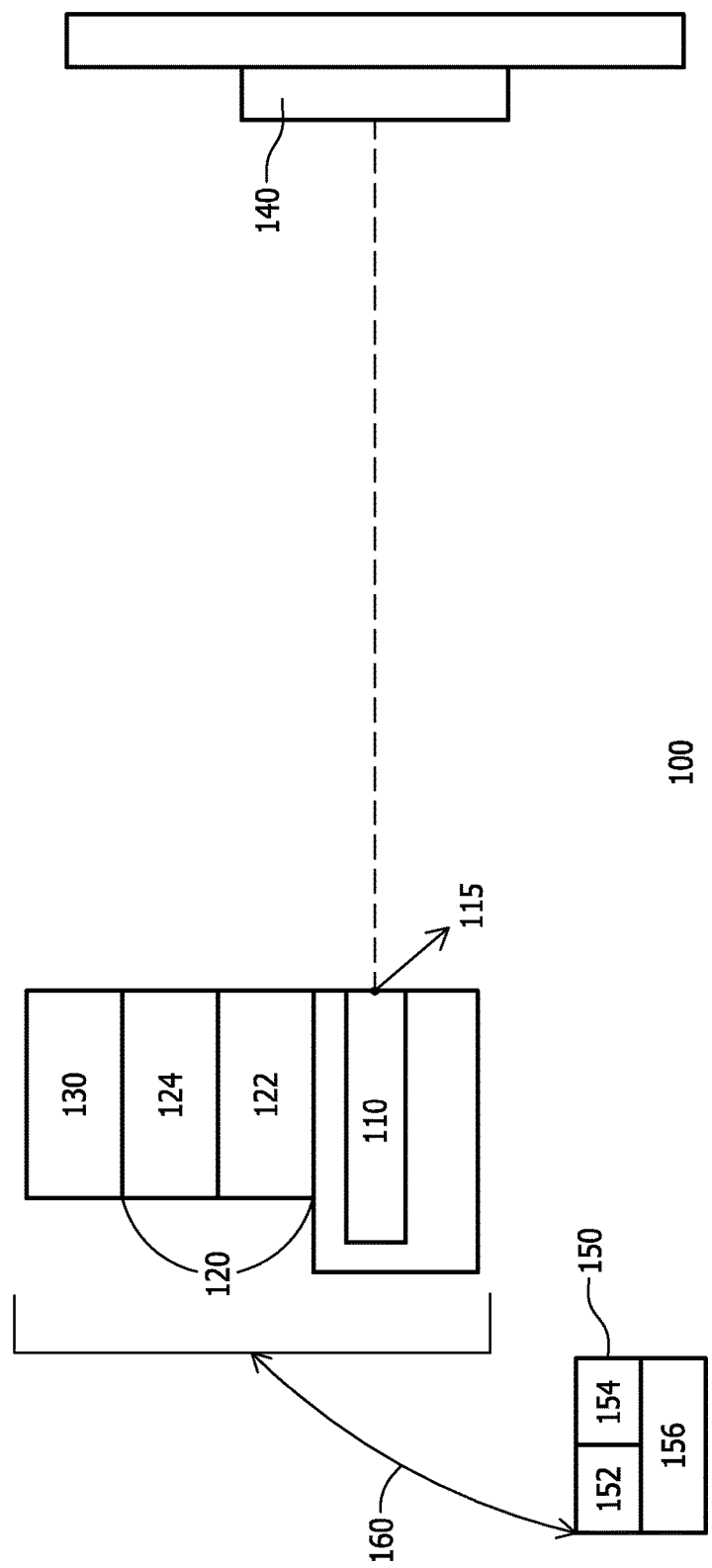
FIG. 1 is a schematic block diagram of a system for improving quality in x-ray imaging according to an illustrative, but non-limiting, exemplary embodiment.

Reference characters in the written specification indicate corresponding items shown throughout the drawing figures.

DETAILED DESCRIPTION OF THE INVENTION

In the following detailed description, numerous specific details are set forth in order to provide a thorough understanding of the invention. The following disclosed embodiments, however, are merely representative of the invention, which may be embodied in various forms. It will be understood by those skilled in the art that the present invention may be practiced without these specific details. Thus, specific structural, functional, and procedural details described are not to be interpreted as limiting. In other instances, well-known methods, procedures, and components have not been described in detail so as to obscure the present invention.

FIG. 1 is a schematic view showing an exemplary embodiment of a system 100 to improve image quality in x-ray of the present invention. The exemplary embodiment of the present invention includes an x-ray tube 110, a depth sensing device 120, a camera 130, an image receptor 140, and a control unit 150. The x-ray tube 110 and the image receptor 140 are positioned to be aligned with each other. The image receptor 140 is preferably positioned in the plane perpendicular to the direction of incident x-rays emitting by the x-ray tube 110; however, the x-ray tube 110 can be positioned differently in other circumstances, e.g., tunnel views of a knee. Preferably, the center of the image receptor 140 is positioned to be aligned with a central ray position 115 of the x-ray tube 110. The central ray position 115 represents the center point of the x-ray tube 110. In addition, the image receptor 140 can be aligned with the depth sensing device 120. The depth sensing device 120 and the camera 130 are preferably mounted on the x-ray tube housing at the level of a focal spot of the x-ray tube 110 or a fixed distance from the focal spot to simplify a source-image distance (SID) geometry and to provide an accurate measurement of a depth from the depth sensing device 120. The SID represents the depth of the image receptor 140 from the focal spot of the x-ray tube 110. However, it should be understood that the depth sensing device 120 and/or the camera 130 can be placed separately from the x-ray tube 110 depending on the condition of an x-ray room and other factors such as the location of a body part that is being radiographed and the location of the image receptor 140. For example, in an x-ray room where only upright chest radiographs are being taken (which is common in large adult centers), the image receptor 140 can be fixed against the wall of the room. In this instance, the depth sensing device 120 and/or the camera 130 can be mounted separately from the x-ray tube 110. Alternatively, the depth sensing device 120 and/or the camera 130 can be mounted within the x-ray tube housing.

Figure 3:
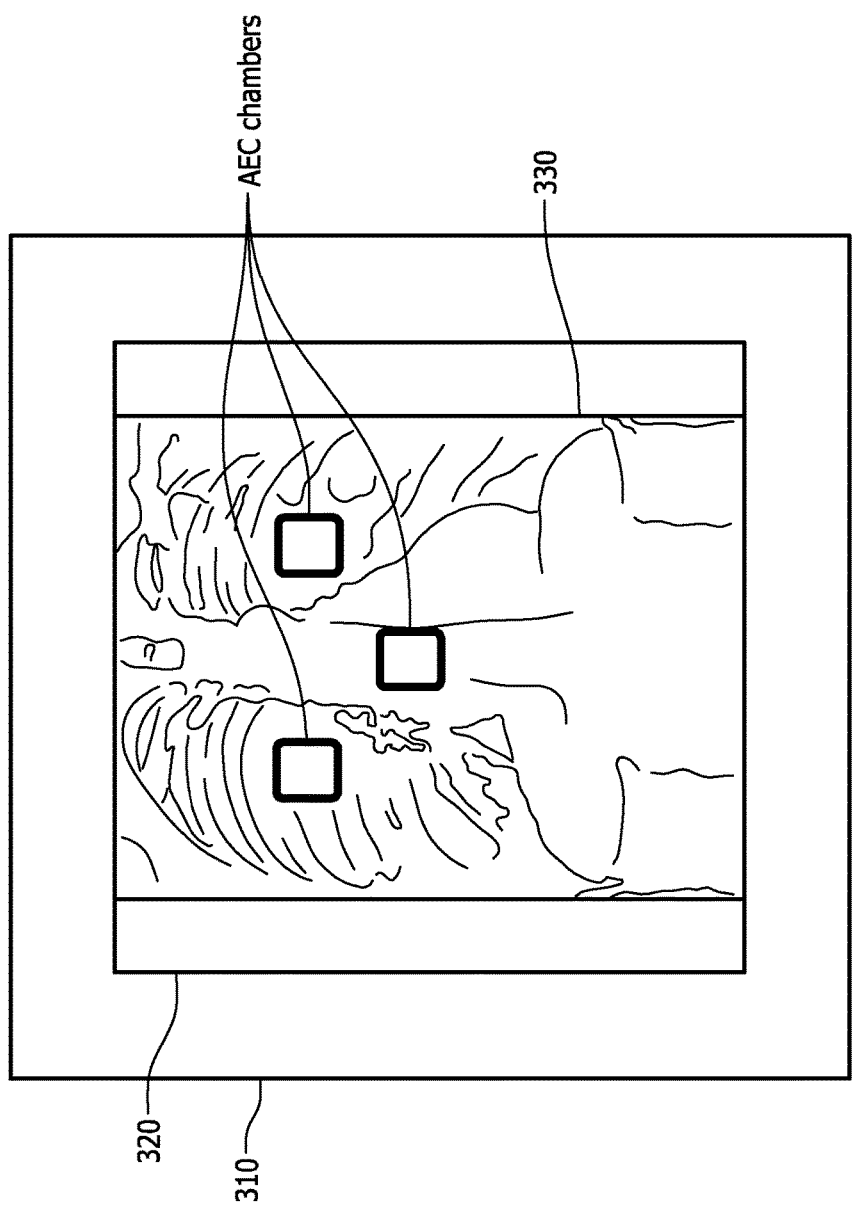
FIG. 3 is a picture of an exemplary embodiment showing a collimated chest radiograph including an overlay of three Automatic Exposure Control (AEC) chambers.

In the exemplary embodiment, the x-ray tube 110 can be any type of standard tube that emits x-rays. Likewise, the image receptor 140 can be any type of standard image receptor that can change x-ray beams into a visible image. Preferably, the depth sensing device 120 is a device capable of detecting a depth by ±1 cm. However, any other depth sensing device having different specifications can also be used if it is suitable to meet the purposes described herein. In one embodiment, one or more Automatic Exposure Control (AEC) chambers can be placed behind the patient but in front of the image receptor 140. Preferably, three AEC chambers are placed behind the image receptor 140 in the same plane perpendicular to the x-ray tube 110 as shown in FIG. 3. The image receptor 320 is encased in a protective enclosure 310 that forms a protective border, e.g., plastic material, around the image receptor 320. In this case, the user has collimated the field side to a side 330 of the targeted body part.

One example of the depth sensing device 120 is an infrared sensor 122. In this example, the depth sensing device 120 is comprised of a plurality of infrared sensors 122 and infrared projector 124 (e.g., MICROSOFT® KINECT® made by the Microsoft Corporation, having a place of business at One Microsoft Way, Redmond, Wash. 98052). Alternatively, other depth sensing devices such as an ultrasonic device or range finders can be used instead of the infrared sensor or in addition to the infrared sensor. In one embodiment, two or more depth sensing devices can be used to aid in determining, for example, an image receptor position when the image receptor 140 is obscured by any object in the room including a patient. In this embodiment, the depth sensing devices can be mounted by the corners of the image receptor to determine the location of the image receptor.

In the exemplary embodiment, the camera 130 can be any standard type RGB camera. In one embodiment, the camera 130 and the depth sensing device 120 can be manufactured as a single product, for example, MICROSOFT® KINECT®.

In the exemplary embodiment, the control unit 150 can be any standard computer or workstation with sufficient computational and network-connectivity capabilities to interface with the x-ray tube 110, the depth-sensing device 120, the camera 130, and/or the image receptor 140. In one embodiment, the control unit 150 can be a mobile device such as a smartphone, tablet computer, laptop, controller, processor, or the like. The control unit 150 comprises a display device 152 and a memory 154. The control unit 150 is operated by software program 156. The software program 156 can be written in C/C++, Java, or any other applicable programming language. In the exemplary embodiment, the software program 156 is written using MICROSOFT® WINDOWS® SDK software development kit; however, it should be understood that this is provided only as an example and should not be used to limit the scope of the present invention. The software program 156 is designed to integrate with the camera 130, the depth sensing device 120, and/or the x-ray tube 110.

The control unit 150 can be connected to the x-ray tube 110, the depth sensing device 120, the camera 130, and/or the image receptor 140 through a data communication link 160. The data communication link 160 can be an inside network or outside network, e.g., the Internet. The data communication link 160 can be any network suitable for the transmission of electronic data. In another embodiment, the data communication 160 is connected to a third party database (not shown) for data transmission.

In operation, the control unit 150 receives an order from a medical staff (e.g., physicians, nurses, etc.). The order can be electronically received via the data communication link 160 or manually delivered to a user (e.g., x-ray technologist) of the system 100. In the exemplary embodiment, the order specifies which body part should be examined. Once the order is received, the user positions a patient between the depth sensing device 120 and the image receptor 140 such that the body part specified in the order is aligned between the depth sensing device 120 and the image receptor 140. The depth sensing device 120 is configured to measure a depth (or distance) between the depth sensing device 120 and the image receptor 140. For example, the infrared projector 124 emits infrared beams to the image receptor 140 and the infrared sensor 122 detects beams reflected by the image receptor 140. The depth sensing device 120 uses the reflected beams to calculate a distance between the x-ray tube 110 and the image receptor 140. The measured distance is used to triangulate the relationship of the AEC chambers of the image receptor 140. In the same manner, the depth sensing device 120 measures a depth of the body part by measuring a distance between the depth sensing device 120 and the body part. This depth can be stored as depth reference data in the memory 154. The control unit 150 then uses the depth reference data (D2) and the measured depth (D1) of the image receptor 140 to calculate a thickness (T) of the body part (as shown in FIG. 2A). In the exemplary embodiment, the control unit 150 is configured to subtract the depth represented by D2 from the depth represented by D1 in order to calculate the thickness (T) of the body part. The calculated thickness of the body part can be stored in the memory 154. Depths of other objects in the field view of the camera 130 can also be calculated using the same method. The control unit 150 and/or the display device 152 are configured to generate a depth map of the image of the objects that are in the field view of the camera 130 as discussed in further detail below with reference to FIG. 7 and FIG. 9.

In one embodiment, the image receptor 140 can be a dummy unit, which has a flat surface that can serve as a base canvas for measuring a depth. In this embodiment, no actual exposure of x-rays is needed. The depth sensing device 120 measures the thickness of a patient's body using a depth of the dummy unit from the depth sensing device 120. The thickness data can be used to determine an optimal level of x-ray exposure for the specified body part.

Figure 2B:
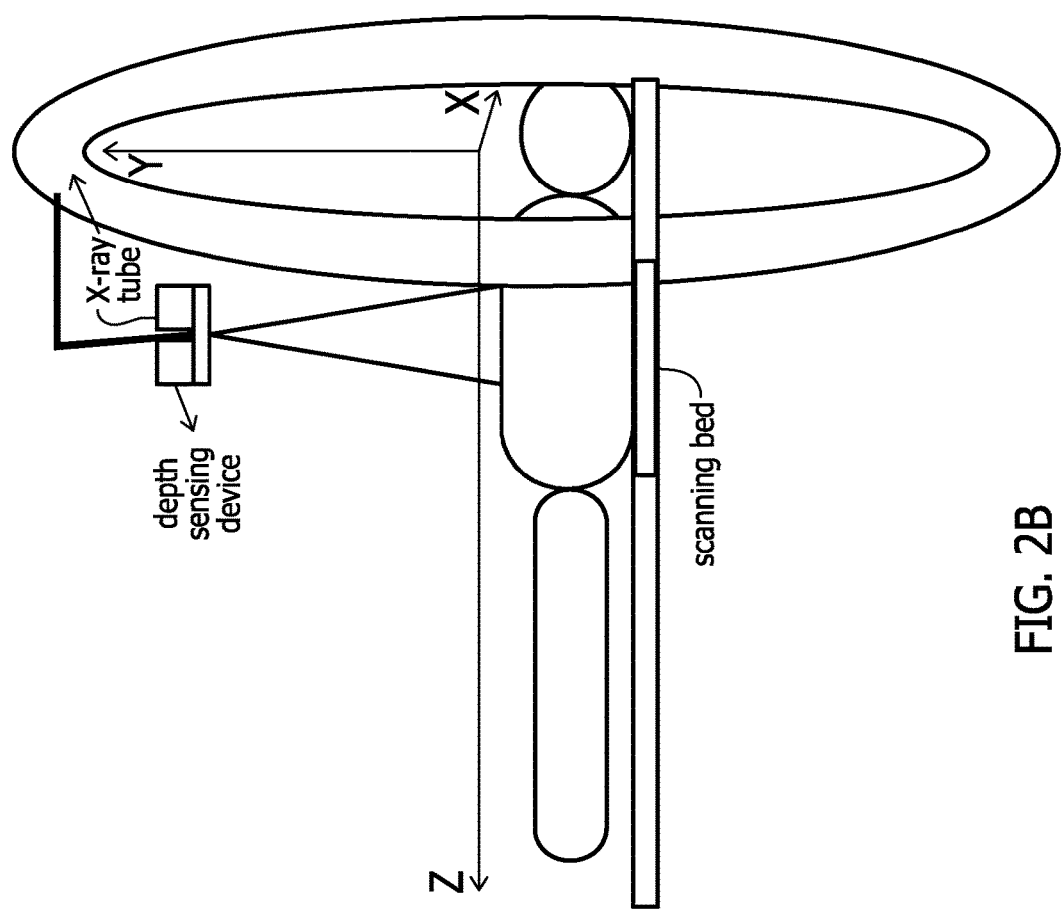
FIG. 2B is a schematic block diagram of an exemplary embodiment measuring a circumference of a patient's body using a Computerized Tomography (CT) scanner.

In one embodiment, the depth sensing device 120 can be configured to measure the circumference of the body part when a Computerized Tomography (CT) scanner is used concurrently with the present invention as shown in FIG. 2B. In FIG. 2B, the depth sensing device 120 can be mounted inside the donut of a CT scanner to determine the circumference of the body part. Additionally, the camera 130 can be mounted on the top of the donut of the CT scanner. The depth sensing device 120 can be used to aid in positioning the patient at the isocenter of the donut of the CT scanner. In the exemplary embodiment, the x-ray tube 110 is built into the donut of the CT scanner. However, other locations for the x-ray tube 110 in conjunction with the depth sensing device 120 are potentially possible. Alternatively, the depth sensing device 120 and/or the camera 130 can also be built into the housing of the x-ray tube 110 or the donut of the CT scanner. The depth sensing device 120 measures a depth between the depth sensing device 120 and the scanning bed on which the patient is lying. Alternatively, instead of directly measuring the depth of the scanning bed, the height of the scanning bed can be obtained from a Radiation Dose Structured Report (RDSR) or Modality Performed Procedure Step (MPPS) connect. The depth sensing device 120 measures a distance between the depth sensing device 120 and the body part and then subtracts it from the distance between the depth sensing device 120 and the scanning bed to calculate a depth of the body party. The width of the body part can be estimated when the distance between the scanning bed and patient depth approaches zero. The calculated depth and width of the body part are used to measure a circumference of the body part. The circumference and geometry information can be used to compute the optimum kV, mA, scanning speed and other technical factors instead of using a localizer with associated radiation.

In the exemplary embodiment, the thickness and/or the circumference of the patient's body can be used to determine an optimal level of x-ray exposure for the body part as further discussed below.

In one embodiment, the optimal level of x-ray exposure for the body part can be further used for determining a patient geometry when a fluoroscopy is concurrently used with the present invention. In this embodiment, the patient geometry can be used for determining a patient entrance exposure. In addition, the control unit 150 is configured to monitor a peak skin dose in real time to minimize x-ray exposure and notify the user when certain pre-defined warning levels are reached. Data concerning the output and position of the x-ray tube 110 can be provided retrospectively by a Radiation Dose Structured Report (RDSR) or Modality Performed Procedure Step (MPPS). In this embodiment, the control unit 150 provides patient geometry and position relative to the x-ray tube 110 focal spot. This information can be used to display a dose distribution map and peak skin dose estimate.

Figure 4:
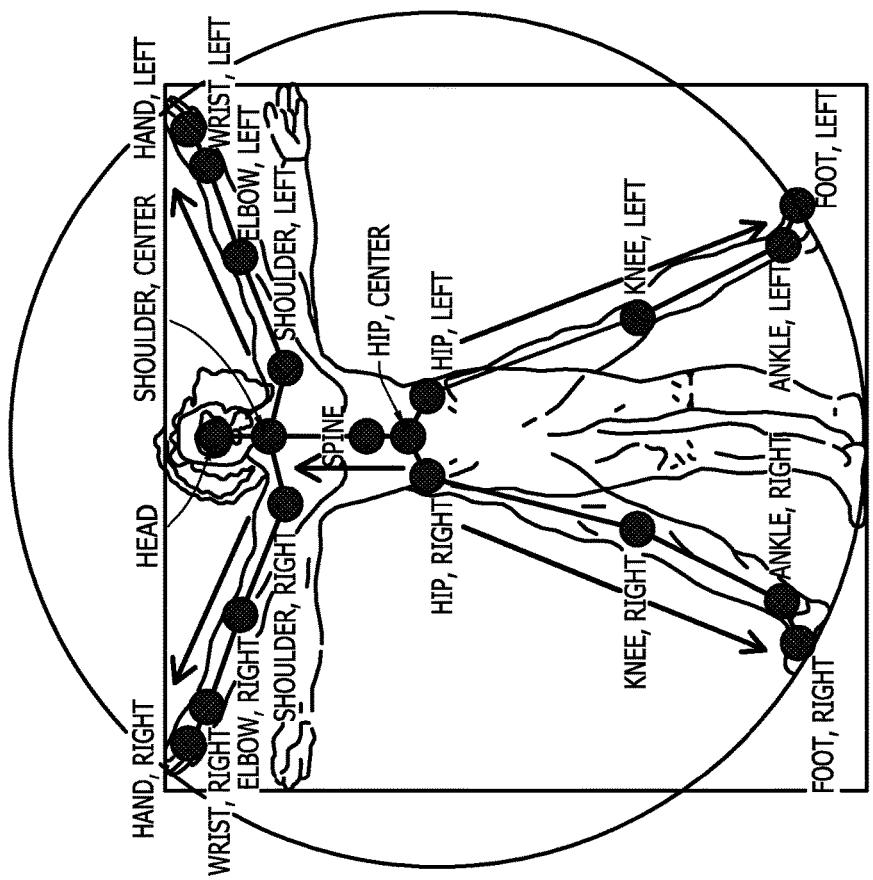
FIG. 4 is a drawing of an exemplary embodiment showing the defined joints of Microsoft Kinect.
Figure 7:
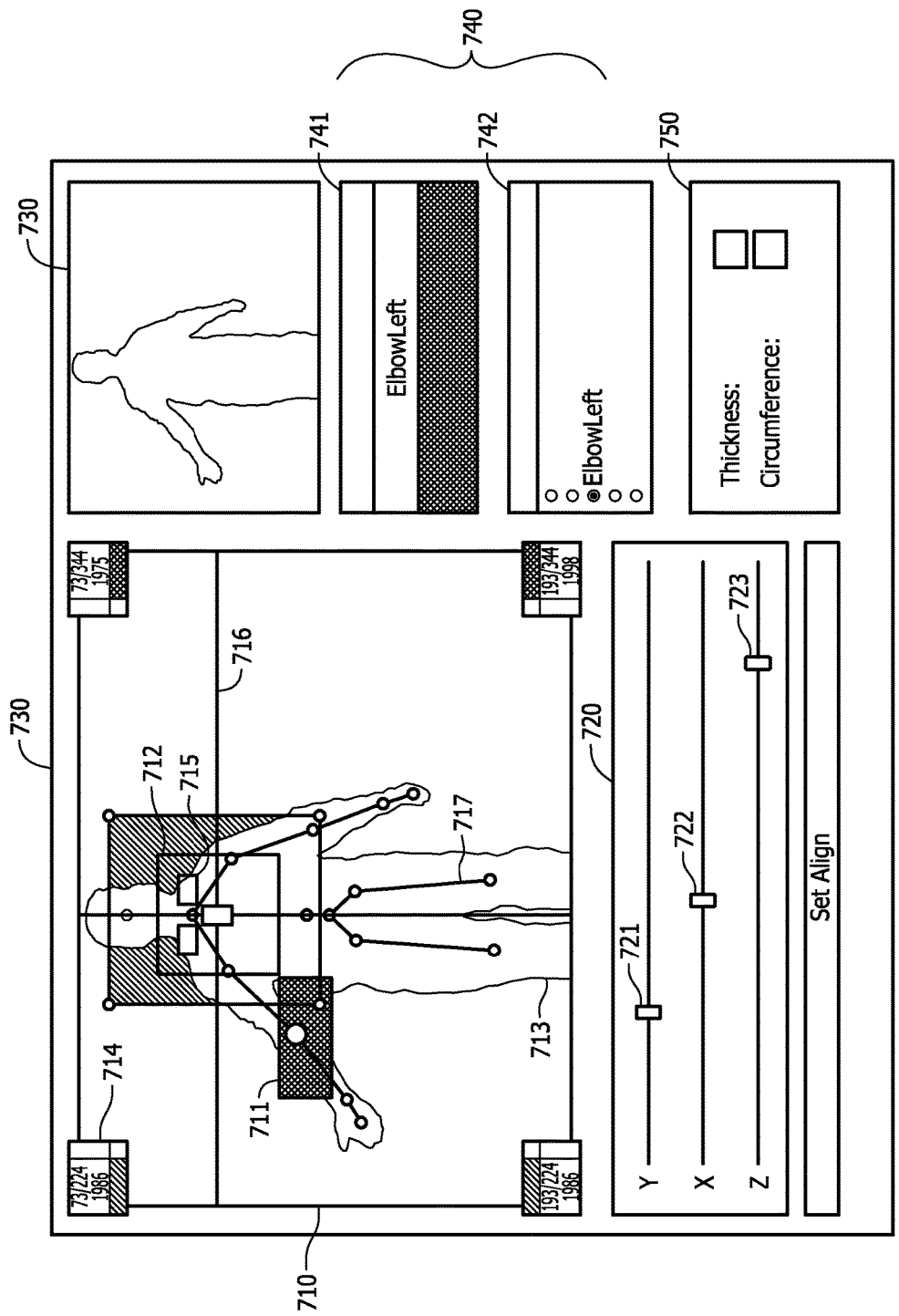
FIG. 7 illustrates a display screen of a system for improving quality in x-ray imaging according to an illustrative, but non-limiting, exemplary embodiment.

In the exemplary embodiment, the display device 152 is configured to display the patient's body concurrently with a skeleton frame (as shown in FIG. 7). The skeleton frame comprises a plurality of joints of the body. These joints can be either pre-defined or user-defined. With respect to the pre-defined joints, the display device 152 can be configured to import any available pre-defined joints such as the one used by MICROSOFT® KINECT®. An example of joints used by MICROSOFT® KINECT® version 1.0 is shown in FIG. 4. With respect to the user-defined joints, the user is enabled to define joints, for example, fingers and toes, which can be created to form the skeleton frame. Body parts can be a single joint or part, or composed of two or more joints or parts. For example, an elbow is a single joint. A forearm would include the elbow joint and wrist joint. A chest may include the shoulders, lower cervical spine, and upper abdomen. In one embodiment, two or more joints can be combined as needed to define a certain body part. In another embodiment, the joint or part selection can be customized for each patient region or for a clinical site.

In the exemplary embodiment, the camera 130 is configured to capture one or more frames of the patient or patient's body. The camera 130 and/or the control unit 150 are configured to identify the body part specified by the order when the order is received. The control unit 150 is configured to control the display device 152 to display the captured body part of the patient's body in a form of the skeleton frame. The identified body part can be highlighted with a targeted body part field such that the user can easily recognize which body part has been identified. If the identified body part is not centered, the display device 152 alerts the user of such misalignment as discussed in further detail below with reference to FIG. 7.

In a typical x-ray environment, the technologist stands by a control panel remote to the patient and at an angle to the patient when actually taking the radiographic image. It is difficult to see if the patient is moving. In the exemplary embodiment, after the body part is identified, the system 100 can determine its motion by using frame subtraction, e.g., by comparing one or more current frames with one or more previous frames captured by the camera 130. If any motion is detected, the system 100 alerts the user of such motion as discussed in further detail below with reference to FIG. 7.

In one embodiment, the system 100 can determine the phase of respiration. For example, when taking images of chest, it frequently is desirable to obtain in deep inspiration for routine chest radiographs. Occasionally, an image in expiration or mid inspiration may be needed. The system 100 can determine the phase of respiration to appropriately time the radiograph or confirm the phase of respiration before taking the image. In another embodiment, the system 100 can be configured to determine an abdomen movement or any joint movement of the patient's body.

The display device 152 is configured to display a targeted body part field. In the exemplary embodiment, the targeted body part field automatically highlights and tracks the patient's body part to be imaged. For example, the targeted body part field is automatically adjusted by the display device 152 to follow the patient's body when the patient moves. When the body part is appropriately centered on the image receptor 140, the user is alerted. The targeted body part field and the body part to be imaged are overlaid to confirm proper collimation (as shown in FIG. 7). The user can adjust the outer boundaries of the targeted body part field to adjust their respective locations when needed as discussed in further detail below with reference to FIG. 7. For example, the user centers the body part of interest on the image receptor 140 within the targeted body part field. The body part to be exposed may be smaller than the size of the image receptor 140 or the targeted body part field. The user can narrow or adjust the targeted body part field so that the body part can be aligned with the targeted body part field.

The display device 152 is also configured to display an image receptor field. The image receptor field comprises an overlay of a plurality of the AEC chambers and a plurality of axes that are used to center the body part to be imaged as discussed in further detail below with reference to FIG. 7. In the exemplary embodiment, three AEC chambers are used; however, it should be understood that any number of AEC chambers can also be used if desired. The AEC chambers are used to control the amount of radiation that exposes an x-ray imaging plate (not shown) and terminate the exposure at that point, a pre-determined exposure. The AEC chambers are placed behind the image receptor 140 in the same plane perpendicular to the direction of incident x-rays and at least one of the AEC chambers is centered relative to the center point of the image receptor 140. In this way, the overlay of the AEC chambers automatically accounts for the source-image distance (SID) as well as a live picture of the patient. The location of the chambers can be configured specifically for the location of the AEC based on manufacturer. In one embodiment, instead of using AEC chambers, the user can manually set the system 100 to terminate the exposure.

When the user centers a patient, the patient's body necessarily obscures the outlines of the AEC chambers. It can be difficult to position the intended anatomy over the respective chambers. For example, in chest imaging, the lateral of the image receptor 140 should be under the lungs while the center is positioned under the mediastinum. This task is tedious and inaccurate when the patient obscures the technologist's view of the chambers. Additionally, when the technologist leaves the room to take the exposure, the patient may have moved without the technologist seeing the movement, and is no longer centered appropriately. By displaying the overlay of the AEC chambers, the technologist can check and verify correct alignment of the patient's body.

The display device 152 is also configured to display the skeleton frame, the targeted body part field, the overlay of the body part to be imaged, the image receptor field, and the depth map simultaneously (as shown in FIG. 7). Further, the display device 152 can be configured to display the skeleton frame, the targeted body part field, the overlay of the body part to be imaged, the image receptor field, and the depth map in real time. In the exemplary embodiment, the image receptor field can be overlaid on the overlay of the body part to be imaged. The targeted body part field can be overlaid on the overlay of the body part to be imaged.

Figure 5:
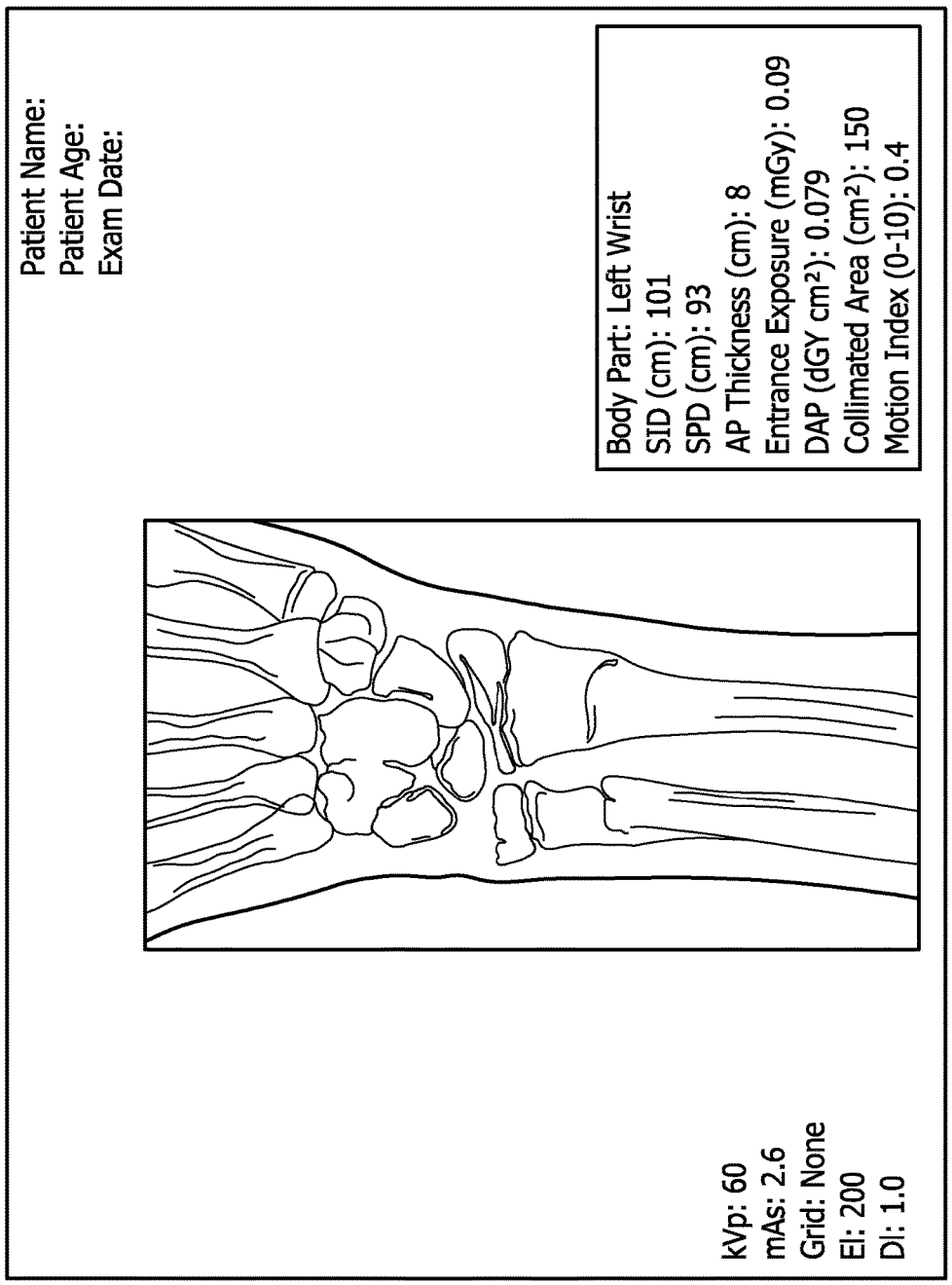
FIG. 5 is a picture of an exemplary embodiment of an x-ray image which includes the thickness of a patient's body part.

The display device 152 can also be configured to display the thickness and/or circumference information of the patient's body, preferably, in real time. Once the user confirms positioning, centering, collimation, and motion, the control unit 150 displays the thickness and/or circumference data. The thickness of the identified body part is used to set an optimal level of x-ray exposure in the given circumstances. In the exemplary embodiment, the control unit 150 is configured to generate an x-ray image, which contains a set of information for the user to determine an appropriate amount of x-ray exposure for the identified body part. FIG. 5 shows an example of such image. In FIG. 5, the image shows, among other things, that the identified body part is a "Left Wrist" and the measured SID is 101 cm. This image can be stored electronically in the memory 154 for future reference. Alternatively, the circumference data can be included in the report in addition to or instead of the thickness data.

In the exemplary embodiment, the thickness and/or circumference data can also be transmitted to a third party database for quality control via the data communication link 160. Other information may be exported to a quality control program such as the dose-area product and information regarding the technique (e.g., kVp, mAs, added filtration, grid, focal spot, SID). The information can be used to revise the technique chart to minimize the variation of the group of patients over time. For example, the information can be used to generate technique selection that creates an optimal amount of x-rays for the identified body part. The parameters used to control an x-ray tube, such as kilovoltage (kVp), milliamperage (mAs), and seconds can be optimized to generate the optimal amount of x-rays for the identified body part.

In an embodiment in which a Computed Tomography (CT) scanner is used, the AEC software algorithm determines the optimum technique from a localizer image using radiation. With the depth sensing device 120, a circumference can be calculated prior to the CT scan in order to calculate the mA and kV output and organ dose distribution. Further, a circumference of the body part can be used for calculation of standard dose metrics such as size-specific dose estimate (SSDE), CT dose index (CTDI), and effective dose.

In the exemplary embodiment, the thickness and/or circumference data can be stored or exported in accordance with a Digital Imaging and Communications in Medicine (DICOM) standard. Currently, there is a tremendous variation in radiographic technique for the same body part, both within an imaging center among technologists and between centers. One of the important determinants for a body part is thickness. In the exemplary embodiment, the thickness data can be imported into one of the headers of a DICOM object as shown in FIG. 6. FIG. 6 shows an example of DICOM header fields that can be used to create a DICOM Structured Report (SR). For example, unknown fields of DICOM headers can be used to store thickness data 610. In addition, known fields of DICOM headers can be used to store information such as the examined body part ("Left-Wrist" 620), a dose-area-product ("0.1266" 630), etc. Similarly, the circumference data can be incorporated into one of the DICOM headers.

DICOM Structured Reports compile the technique information as well as patient exposure data. There are recommended exposure value ranges that each manufacture suggests for their equipment. By combining the thickness data with the DICOM information, the exemplary embodiment can utilize and track any information stored in the DICOM headers. In one embodiment, real-time feedback of the DICOM information can be provided. For example, in an intensive care unit where daily chest radiographs are being taken, a notification of prior techniques and suggested modification can be utilized for subsequent imaging to obtain an optimum exposure of x-ray by using the combined information stored in DICOM SRs. Another example is a patient having multiple views of the same body part, such as taking bilateral AP and oblique views of the hands. After the first x-ray image, from the thickness data and resulting exposure data the technique can be adjusted to give an ideal exposure. Furthermore, combining the body part thickness with the DICOM SR data can be used to refine technique charts, the suggested technique for the particular body part and thickness thereof, which hospitals use, to reduce variability among patients. For quality control purposes, many parameters are required to verify appropriate technique: body part thickness, body part circumference, patient entrance exposure, image receptor entrance exposure, and technique (e.g., kVp, mAs, etc.). The exemplary embodiment of the system 100 provides critical data related to patient size and provides a more meaningful quality control tool then conventional monitor technique and exposure.

In one embodiment, the thickness and/or circumference data stored in the DICOM headers can be merged into one database. In another embodiment, the information stored in the DICOM headers can be imported into the memory 154 of the control unit 150 or any database electronically accessible by the control unit 150. The system 100 allows the user to perform a quality control of the amount of x-rays emitted based on the thickness data or circumference data and the information stored in the DICOM headers.

In one embodiment, the control unit 150 can be configured to generate a report or data automatically showing the selected technique. Alternatively, the control unit 150 can be configured to allow the user to generate the same manually.

FIG. 7 is an exemplary display screen of the display device 152 of FIG. 1.

The exemplary display screen comprises a main screen 710, an alignment control panel 720, a video screen 730, a joint motion monitoring screen 740, and a data section 750.

The main screen 710 further comprises a targeted body part field 711, an image receptor field 712, an overlay of a patient's body 713, and coordinates 714. In the exemplary embodiment, the image receptor field 712 comprises an overlay of one or more AEC chambers 715 and a plurality of axes 716. The AEC chambers are fixed in location relative to the image receptor 140. The center point of the axes 716 represents the center point of the image receptor field 712. The center point of the image receptor field 712 can be adjusted by the user to be aligned with the central ray position 115 (or the center point of the image receptor 140) so that the body part can be properly aligned with the x-ray tube 110. The axes 716 comprise an x axis, y axis, and z axis (not shown). In the exemplary embodiment, the x-axis represents a horizontal coordinate (left/right), the y-axis represents a vertical coordinate (up/down), and the z-axis represents a depth (near/far). The image receptor field 712 defines the size of the image receptor 140. The targeted body part field 711 defines an area where x-ray exposures are expected to be collimated.

The overlay of a patient's body 713 represents an actual body of a patient. The overlay of a patient's body 713 comprises a skeleton frame 717. The skeleton frame 717 represents the pre-defined joints of the patient and is concurrently displayed together with the overlay of the body. The body part to be imaged, comprised of one or more joints, is highlighted on the skeleton frame.

The coordinates 714 represent the coordinates of the four corners of the image receptor field 712. In the exemplary embodiment, the x, y, and z-axes coordinates of the four corners of the image receptor field 712 are displayed as the coordinates 714 of FIG. 7.

In the exemplary embodiment, the main screen 710 presents depth information of objects (e.g., depth map) in the field view of the camera 130. The software program 156 of the control unit 150 is configured to calculate color gradients according to the measured distance between the depth sensing device 120 and an object and generate appropriate input signal for the display device 152 to color the object or any part thereof with the associated color gradient. For example, the depth (D1 of FIG. 2A) representing the distance between the depth sensing device 120 and the image receptor 140 can be colored green and can serve as a base depth for calculating different depths. As such, any object or body or any part thereof having the same depth as D1 would be colored same. Objects that are not in the same distance from the depth sensing device 120 as D1 can be displayed with different colors. For example, the body part of the patient can be colored brown as shown in FIG. 7 in order to distinguish the body part easily from the image receptor 140 and the targeted body part field 711. This confirms that the patient is standing between the x-ray tube 110 and the image receptor 140. If the patient walks toward the depth sensing device 120 then the color of the body part would be changed in proportion to a distance between the patient and the depth sensing device 120. It should be understood that the system 100 can be configured to display depth information based on a non-color indicator as well. For example, the system 100 can be configured to generate audible sound telling how far an object is distanced from the depth sensing device 120 or whether an object is properly aligned between the x-ray tube 110 and the image receptor 140.

In the exemplary embodiment, the system 100 can be configured to display a numerical value representing an actual distance between the depth sensing device 120 and an object.

The alignment control panel 720 comprises a control panel that allows the user to position the image receptor field 712 in a proper location. For example, the user can move a "Y-UP/DOWN SLIDER" button 721 to adjust the y-axis of the center point of the image receptor field 712. The user can either move up or down the y-axis to adjust a vertical coordinate of the center point of the image receptor field 712. Likewise, the user can adjust the x-axis and z-axis by moving "X-LEFT/RIGHT SLIDER" 722 and "Z-NEAR/FAR SLIDER" 723 buttons respectively. In the exemplary embodiment, these buttons are shown as a sliding-scaling button; however, it should be understood that these buttons are shown only as an example and should not be used to limit the scope of the present invention. Any other buttons or user interfaces that are applicable to meet the purposes described herein can also be used. The alignment control panel 720 additionally comprises a "SetAlign" button, which enabled, fixes the z-axis of the image receptor field 712, i.e., fix the depth of the image receptor field 712. Once the z-axis is fixed, the user then can adjust the x-axis and y-axis of the image receptor field 712.

In the exemplary embodiment, after the user completes the positioning or calibrating of the image receptor field 712, the alignment control panel 720 is no longer used.

In one embodiment, the user is enabled to adjust the size of the targeted body part field 711. For example, when an order specifies a body part that is larger/smaller than the current targeted body part field 711, the user can expand/narrow the targeted body part field 711. The user may be allowed to directly move each corner or side of the targeted body part field 711 and re-position the same at a location where the user wants them to be. The user may also be allowed to define a new size for the targeted body part field 711 (e.g., type in numerical values). In this manner, the user is enabled to change the shape or size of the targeted body part field 711 as shown in FIG. 7. Preferably, the user adjusts the targeted body part field 711 in accordance with actual collimation of the x-ray tube 110 such that the targeted body part field 711 accurately represents an area where x-rays emitted by the x-ray tube 110 are collimated. In the exemplary embodiment, the targeted body part field 711 can be highlighted with colors with green (the body part is centered), yellow (the body part is slightly off centered); and red (the body part is not centered). However, other methods of highlighting can be used such as flagging, blinking, generating audible sound, and displaying numerical scale or text.

The video screen 730 displays a video stream of frames captured by the camera 130. In the exemplary embodiment, the video stream is displayed in real time. The user can check the body part positioning.

The joint motion monitoring screen 740 comprises a monitoring section 741 and a selection section 742. In the exemplary embodiment, the monitoring section 741 provides an identification of a joint(s) that has been selected by the user or requested to be examined by a medical staff. For example, as shown in FIG. 7, the monitoring section 741 provides textual information, which explains that the currently identified body part is an "ElbowLeft" 742. The main screen 710 concurrently highlights the identified joint, e.g., left elbow is highlighted with the targeted body part field 711 as shown in the main screen 710. Further, if the joint is not centered or not aligned properly relative to the center point of the image receptor 140, the system 100 alerts the user. In the exemplary embodiment, the joint is colored green (centered), yellow (slightly off centered), and red (not centered). Similarly, the monitoring section 741 alerts the user if the identified joint is moved by coloring: red (moved), yellow (slightly moved), and green (not moved). It should be understood that other methods of highlighting or alerting can be used such as flagging, blinking, generating audible sound, and displaying numerical scale or text to alert misalignment or motion. For example, the system 100 can be configured to generate audible sound, which simply tells the user that the identified joint or joints are not centered, and how far they are distant from the central ray position 115. In another example, the system 100 can be configured to generate audible sound, which tells the user that the patient has moved the identified body part and how far the identified body part has moved since the last positioning.

The selection section 742 provides an interface for the user to select one or more pre-defined joints. In the exemplary embodiment, an order is provided by a medical staff that specifies a body part to be examined. In this instance, the system 100 automatically selects the body part specified in the order. In one embodiment, the user can manually select one or more joints by selecting one of the listed body parts as shown in the selection section 742. In this embodiment, the selection section 742 comprises a radio-selection menu and a scroll down bar; however, it should be understood that any other applicable methods may be used instead of radio-buttons. In the exemplary embodiment, once a body part is selected in the selecting section 742, the system 100 is configured to update automatically the monitoring section 741 in accordance with the selected body part. For example, the monitoring section 741 displays the selected body part and shows the movement of the selected body part automatically once the body part is selected at the selection section 742.

The data section 750 displays the thickness data and the circumference data of the identified body part.

Figure 8:
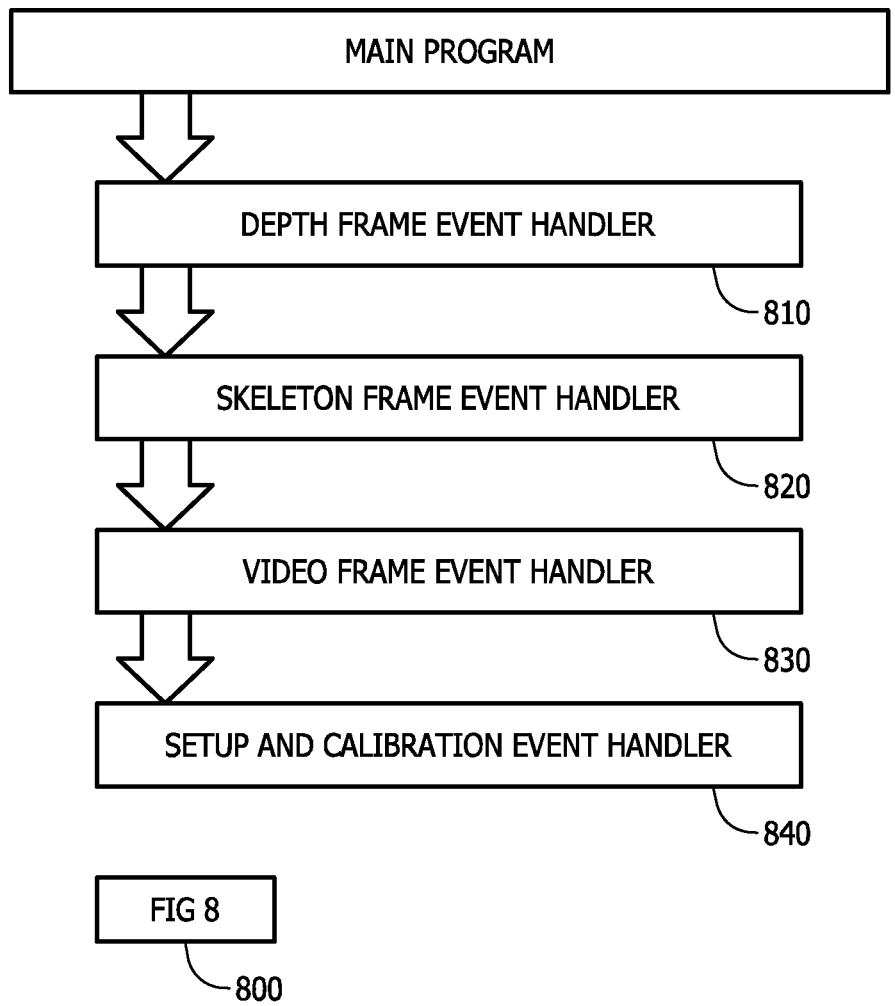
FIG. 8 is a flow chart of a method for generating the exemplary display screen of FIG. 7.

In operation, the control unit 150 is configured to run the software program 156 to control the display of the system 100. FIG. 8 is a flowchart showing an exemplary method of generating the exemplary display screen of FIG. 7.

In the exemplary embodiment, the software program 156 represents a Microsoft Windows program written in C# that used Windows Presentation Foundation for its GUI. The software program 156 uses the Kinect DLL to receive data streams such as depth, skeleton, and video. However, it should be understood that this is provided only as an example and the software program 156 can be written using other sources of GUI. In the description of the flowcharts, the functional explanation marked with numerals in angle brackets, <nnn>, will refer to the flowchart blocks bearing that number.

At step <810>, the control unit 150 triggers the operation of a depth frame event handler. The depth frame event handler manages the display of depth information as discussed in further detail below with reference to FIG. 9.

At step <820>, the control unit 150 triggers the operation of a skeleton frame event handler. The skeleton frame event handler manages the display of the overlay of the patient's body 713 and the skeleton frame 717 as discussed in further detail below with reference to FIG. 10.

At step <830>, the control unit 150 triggers the operation of a video frame event handler. In the exemplary embodiment, the video frame event handler manages the display of the video screen captured by the camera 130. Preferably, the video frame event handler is configured to manage the display of the video screen 730 of FIG. 7.

At step <840>, the control unit 150 triggers the operation of a setup and calibration event handler. The setup and calibration event handler manages the display of other components in the display screen of FIG. 7 such as the alignment control panel 720.

Figure 9:
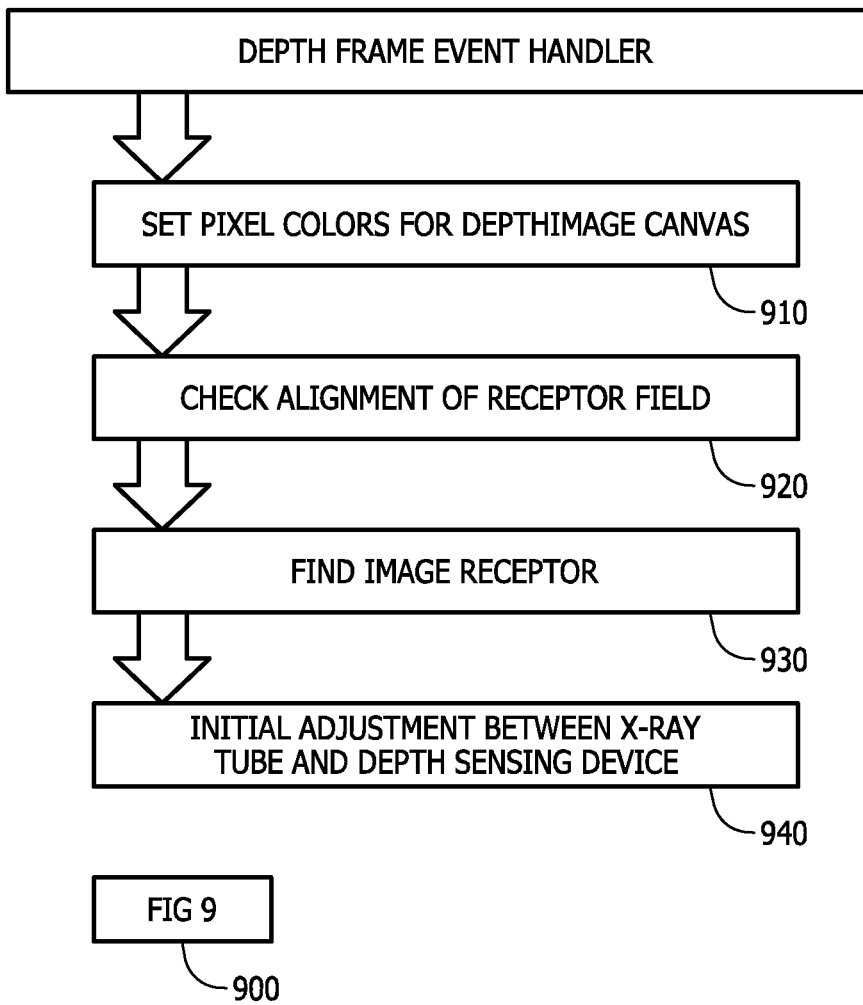
FIG. 9 is a flowchart of a method for managing the depth frame handler of FIG. 8.

FIG. 9 is a flowchart showing an exemplary method of managing the depth frame handler of FIG. 8. At step <910>, the depth frame event handler is configured to set pixel colors for depth image canvas. In the exemplary embodiment, the surface of the image receptor 140 serves as depth image canvas. The depth sensing device 120 is configured to measure a depth by pixels. For example, the depth frame event handler is configured to measure depths of 640×480 pixels, e.g., 30 times a second. Alternatively, different pixel sizes can be used. The pixel values contain depth in millimeters and personal identifier. The personal identifier is used to identify the depth information of a particular person. For example, the system 100 can be configured to display the depth information of multiple people and the overlays of their skeleton frames at the same time. In this instance, the system 100 uses the personal identifier to identify each individual. The depth sensing device 120 preferably measures a depth (or a distance) from a single point that is distant from the depth sensing device 120. Each point corresponds to a pixel and is treated as a single processing unit for purposes of measuring a depth. Likewise, the surface of the image receptor 140 can be broken down into a plurality of points that correspond to pixels. However, it should be understood that any other method of measuring a depth (not based on pixels) can also be used if it is suitable to meet the purposes described herein.

The depth frame event handler sets a color for the depth image canvas (e.g., the image receptor 140) to display the depth of the image receptor 140. In the exemplary embodiment, the depth image canvas can be set as green, i.e., the surface of the image receptor 140 is colored green. Other objects such as a patient body can be colored differently in order to easily distinguish them from the image receptor 140. For example, the patient body (i.e., pixels corresponding to the patient's body) can be set as brown.

In one embodiment, the depth event handler is configured to set pixel colors based on certain threshold points. For example, objects or body parts that are less than 10 mm in thickness relative to the image receptor 140 can be colored green. Other pixels that are less than 20 mm, but more than 10 mm, in thickness relative to the image receptor 140 can be colored yellow. Other image receptor pixels that are less than 30 mm, but more than 20 mm, in thickness relative to the image receptor 140 can be colored red. Other objects that are not recognizable or that are not needed to be identified for purposes of measuring a depth can be colored white. Lastly, far objects (e.g., objects placed behind the image receptor 140) or close objects (e.g., objects placed near the depth sensing device 120) can be colored grey such that these objects would not be confused with any body part of the patient that needs to be imaged. In one embodiment, a different threshold point can be used instead of the image receptor 140. For example, depths can be measured according to a distance from a certain object or line positioned between the depth sensing device 120 and the image receptor 140. In this embodiment, image receptor pixels are colored in proportion to their distance from that object or line, not from the image receptor 140.

At step <920>, the depth frame event handler checks the alignment of the image receptor field 712. In the exemplary embodiment, the depth frame event handler checks the depth information of each corner of the image receptor field 712. Similar to the image receptor pixels of step 910, the depth frame event handler uses a reference threshold. For example, the depth frame event handler displays with green a coordinate 714, if a corner corresponding to that coordinate 714 is less than 10 mm in thickness relative to the image receptor 140, yellow if less than 20 mm, but more than 10 mm in thickness relative to the image receptor 140, and red if less than 30 mm, but more than 20 mm in thickness relative to the image receptor 140. The depth frame event handler is configured to calculate the x, y, and z coordinates of the four corners of the image receptor field 712 so that the coordinates of such can be displayed as the coordinates 714 of the main screen 710 as shown in FIG. 7. In this way, the user can know whether the image receptor field 712 is centered, and if not, how far the image receptor field 712 is from a desired position. Other methods not using colors can also be used to inform the user of the depth information of the image receptor field 712.

At step <930>, the depth frame event handler finds the image receptor 140. In the exemplary embodiment, the depth frame event handler finds the edges of the image receptor 140 by checking distances. For example, the edges of the image receptor borders can be identified by finding a border line where there is typically a sudden decrease/increase in depth as any points outside of, but adjacent to, the image receptor region would have a depth substantially different from the points that reside on the image receptor 140. After finding the edges, the depth frame event handler computes the depth information of the AEC chambers so that the overlay of the AEC chambers can be displayed concurrently with other information in the main screen 711 as shown in FIG. 7.

At step <940>, the depth frame event handler performs an initial adjustment of the alignment between the x-ray tube 110 and the depth sensing device 120. In the exemplary embodiment, the depth frame event handler calculates a distance between the focal spot of the x-ray tube 110 and the depth sensing device 120 such that this distance can be offset by the depth sensing device 120 when measuring depths of objects.

Figure 10:
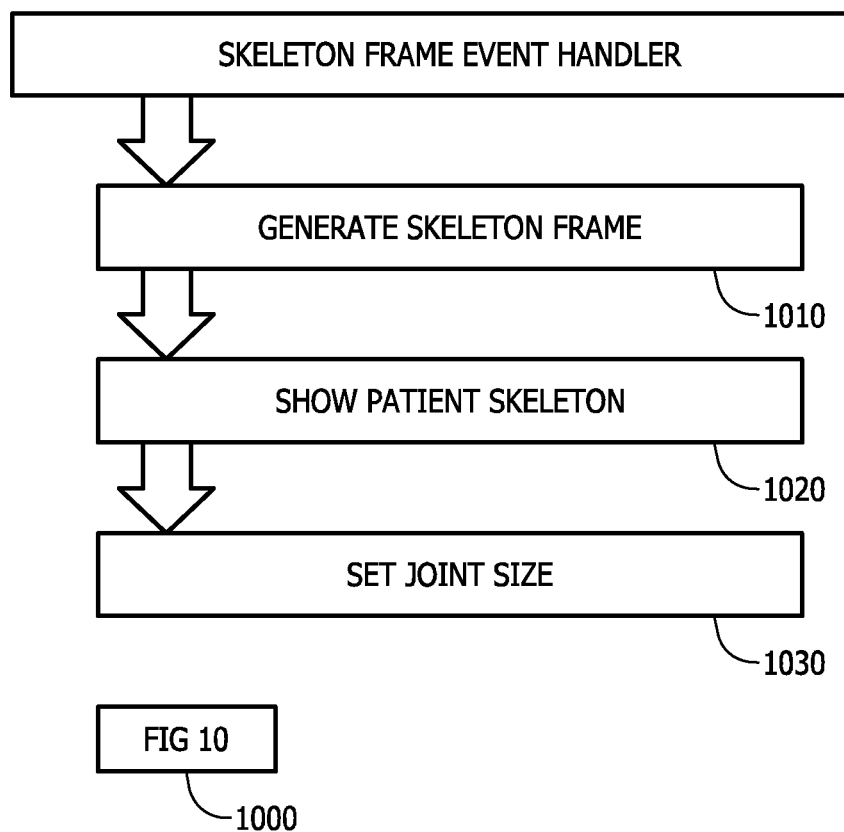
FIG. 10 is a flowchart of a method for managing the skeleton frame event handler of FIG. 8.

FIG. 10 is a flowchart showing an exemplary method of managing the skeleton frame event handler of FIG. 8.

At step <1010>, the skeleton frame event handler generates a skeleton frame, which is comprised of one or more joints of a patient's body. In the exemplary embodiment, the skeleton frame event imports joints from any one of pre-existing joint database or enables the user to define joints for a patient's body as discussed above in FIG. 1. The skeleton frame event handler then calculates depths of each joint in the frame and keeps track of the joint movement and joint depth. The display 750 is configured to show the thickness and/or circumference of the targeted body part to be imaged. The display 750 is also configured to show the body part concurrently with the skeleton frame of the body part.

At step <1020>, the skeleton frame of a patient is displayed. The depths information calculated at step <1010> is used by the display device 152 to display the depths of the joints of the skeleton frame of the body part to be imaged as shown in FIG. 7.

At step <1030>, the skeleton frame event handler sets a joint size. As discussed above in FIG. 1, the size of joints can be defined by the user or can be customized based on any particular need or purpose. The skeleton frame event handler can be configured to import the standard size used in any of the pre-existing joints.

Figure 11:
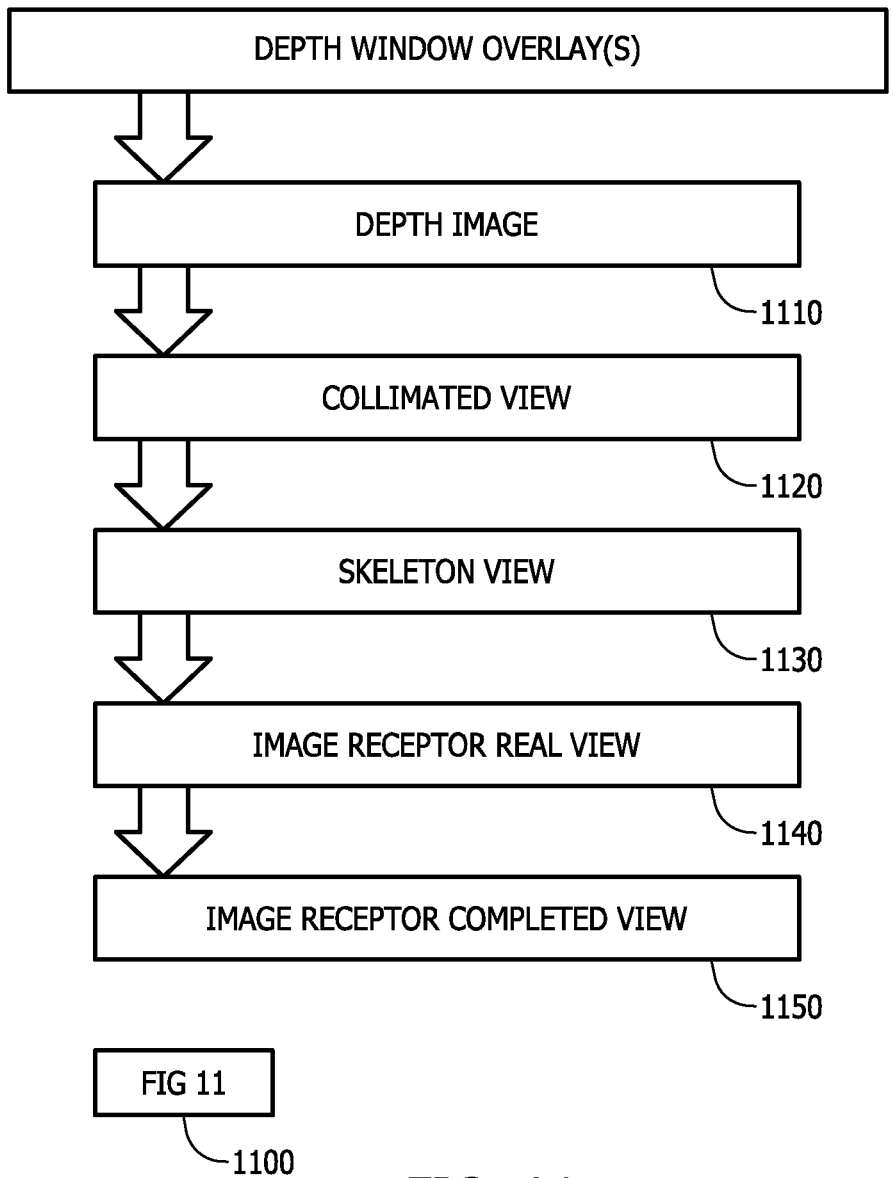
FIG. 11 is a flowchart of a method for displaying the display screen of FIG. 7.

FIG. 11 is a flowchart showing an exemplary method of displaying the display screen of FIG. 7.

At step <1110>, the display device 152 is configured to display a depth image. In the exemplary embodiment, the depth image comprises the depth map of objects that are in the field view of the camera 130.

At step <1120>, the display device 152 is configured to display a collimated view. In the exemplary embodiment, the collimated view comprises the targeted body part field 711, the image receptor field 712, and the coordinates 714.

At step <1130>, the display device 152 is configured to display a skeleton view. In the exemplary embodiment, the skeleton view comprises the overlay of the patient's body 714 and the skeleton frame 717.

At step <1140>, the display device 152 is configured to display an image receptor real view. In the exemplary embodiment, the image receptor real view comprises the video screen of FIG. 7.

At step <1150>, the display device 152 is configured to display an image receptor computed view. In the exemplary embodiment, the image receptor computed view comprises the alignment control panel 720. The user is enabled to align the image receptor field 712 (as discussed further detail above with respect to FIG. 7) so that the image receptor field 712 is properly aligned with the x-ray tube 110.

In the exemplary embodiment, the depth image, collimated view, skeleton view, image receptor real view, and image receptor computed view are concurrently displayed by the display device 152. Additionally, these views can be displayed in real time.

Figure 12:
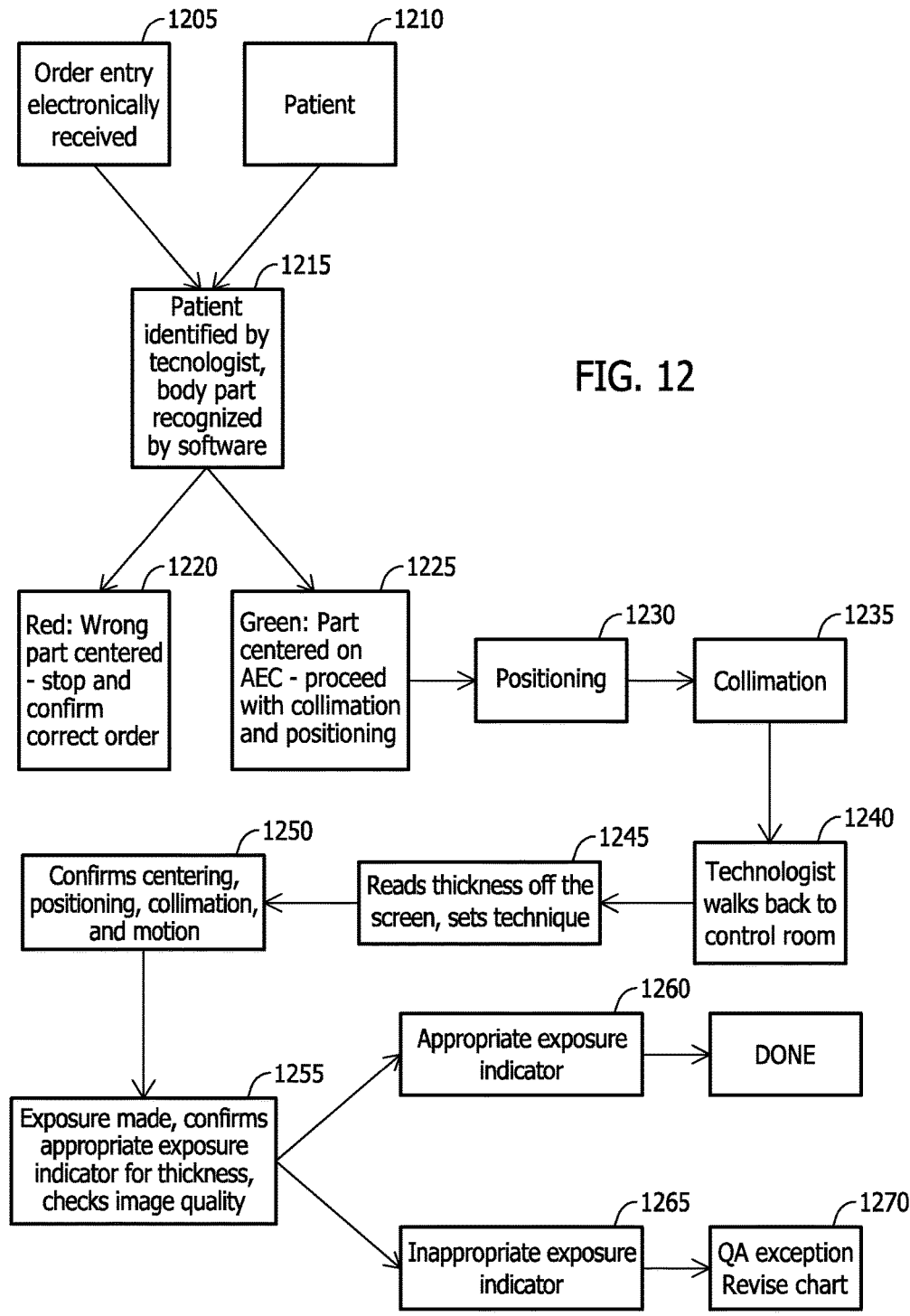
FIG. 12 is a flowchart of a method for improving quality in x-ray imaging according to an illustrative, but non-limiting, exemplary embodiment.

FIG. 12 is a flowchart of a method for improving quality in x-ray imaging.

At step <1205>, an order is received from a medical staff. The order specifies which body part of the patient should be examined.

At step <1210>, the patient is brought by the user (e.g., technologist) to the room.

At step <1215>, the control unit 150 of FIG. 1 identifies the body part specified in the order. The patient is positioned between the x-ray tube 110 and the image receptor 140. At the same time, the patient is positioned appropriately for the examination requested and aligned with the depth sensing device 120 for purposes of measuring depths. Alternatively, the user can manually read the order and identify the body part specified in the order. The control unit 150 highlights the identified body part with the targeted body part field 711 by utilizing one of the followings: coloring, blinking, flagging, generating audible sound, and displaying numerical scale or text.

At step <1220>, if the body part is not centered, the control unit 150 alerts the user that the body part is not centered by utilizing one of the followings: coloring, blinking, flagging, generating audible sound, and displaying numerical scale or text.

At step <1225>, if the body part is centered, the control unit 150 alerts the user that the body part is centered by utilizing one of the followings: coloring, blinking, flagging, generating audible sound, and displaying numerical scale or text.

At step <1230>, if the body part is found not to be centered at step <1220>, the user positions the body part so that the body part is properly centered.

At step <1235>, the control unit 150 provides a display for the user so that the user can check collimation. For example, the display device 152 displays the image receptor field 712. By adjusting the location/alignment of the image receptor field 712, the user is able to define the body part where x-ray exposure will occur. The display device 152 also displays the targeted body part field 711. The targeted body part field 711 tracks the identified body part and thus shows how the body part is positioned in relation to the image receptor field 712 and the AEC chambers 715. The display device 152 is configured to highlight the targeted body part field 711 if the body part is not properly centered. In the exemplary embodiment, the targeted body part field 711 can be colored green (if the body part is centered), yellow (if the body part is slightly off centered), and red (if the body part is not centered).

At step <1240>, the user walks back to a control room.

At step <1245>, the user reads information from the display device 152. For example, the user can read the thickness data or circumference data calculated by the depth sensing device 120 and/or the control unit 150. The user can set technique selection based on the thickness or circumference of the identified body part. An optimal level of x-ray exposure for the identified body part can also be determined based on the given information.

At step <1250>, the user confirms centering, positioning, collimation, and motion of the identified body part. Alternatively, the control unit 150 can be configured to automatically confirm centering, positioning, collimation, and motion of the identified body part.

At step <1255>, the user controls the x-ray tube 110 to emit the determined optimal level of x-rays. In one embodiment, this step can be performed automatically by the control unit 150. The user confirms appropriate exposure indicator for thickness or circumference and checks image quality.

At step <1260>, if appropriate exposure has been made, the whole procedure is ended.

At step <1265>, if appropriate exposure has not been made, then the user conducts a quality check. For example, the thickness and/or circumference data of the body part can be exported to a quality control program such as the dose-are product and information regarding x-ray technique (e.g., kVp, mAs, added filtration, grid, focal spot, SID). This information can be used to revise the technique chart to minimize the variation of the group of patients over time.

While this description focused on radiography, the system and method described herein can be used with any x-ray generating equipment, such as a CT scanner and fluoroscopy, to measure thickness and circumference of a certain body part and patient geometry.

It should be understood that when introducing elements of the present invention in the claims or in the above description of the preferred embodiment of the invention, the terms "have," "having," "includes" and "including" and similar terms as used in the foregoing specification are used in the sense of "optional" or "may include" and not as "required." Similarly, the term "portion" should be construed as meaning some or all of the item or element that it qualifies.

Thus, there have been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications, which do not depart from the spirit and scope of the invention, are deemed to be covered by the invention, which is limited only by the claims that follow.

The invention claimed is:

1. A system for improving quality in projection and tomographic x-ray imaging comprising:
   an x-ray tube emitting x-rays;
   a depth sensing device measuring a depth of at least one body part of a patient, wherein the depth represents a distance between said depth sensing device and the body part;
   a control unit comprising a memory, wherein said memory stores depth reference data that represents the distance between said depth sensing device and the body part, wherein said depth reference data is used to calculate one of a thickness of the body part and a circumference of the body part, and wherein the calculated thickness or circumference is used to determine an optimal level of x-ray exposure for the body part; and a RGB camera identifying at least one body part of the patient, wherein said control unit is configured to display an overlay of the patient's body, wherein the patient's body is displayed concurrently with a skeleton frame comprising a plurality of pre-defined joints of the body, wherein said control unit is configured to alert a user if the identified body part is not centered, wherein said RGB camera is configured to capture a plurality of frames of the patient's body, wherein said control unit is configured to detect a motion of the patient by comparing at least one frame currently captured by said RGB camera with at least one frame previously captured by said RGB camera, and wherein said control unit is configured to alert the user if any motion is detected.

2. The system for improving quality in projection and tomographic x-ray imaging according to claim 1, wherein the motion comprises at least one of the following: a plurality of phases of chest movement during respiration, abdominal movement during respiration, and joint movement of any body part of the patient.

3. A method for improving quality in projection and tomographic x-ray imaging comprising:

measuring a depth of at least one body part of a patient with a depth sensing device, wherein the depth represents a distance between said depth sensing device and the body part;

storing depth reference data in a memory associated with a control unit, wherein the depth reference data represents the depth of the body part;

calculating one of a thickness of the body part and a circumference of the body part using the depth reference data;

determining an optimal level of x-ray exposure of the body part using one of the thickness of the body part and the circumference of the body part;

displaying an overlay of the patient's body with said control unit, wherein the patient's body is displayed concurrently with a skeleton frame comprising a plurality of pre-defined joints of the body;

identifying at least one body part with an RGB camera, wherein a user is alerted if the identified body part is not appropriately centered; and detecting, with said control unit, a motion of the patient by comparing at least one frame currently captured by said RGB camera with at least one frame previously captured by said RGB camera, wherein said RGB camera is configured to capture a plurality of frames of the patient's body, and wherein the user is alerted by said control unit if any motion is detected.

4. A system for improving quality in projection and tomographic x-ray imaging comprising:
an x-ray tube;
an image receptor;
a depth sensing device, wherein said image receptor is positioned to be aligned with said depth sensing device;
a RGB camera; and
a display device, wherein said display device is configured to display a depth-image view, collimated view, and skeleton view, wherein the depth-image view comprises a plurality of pixels, each of which represents a distance between said depth sensing device and each point of said image receptor that corresponds to each pixel, wherein the distance is measured by said depth sensing device, the collimated view comprises a targeted body part field and an image receptor field, the skeleton view comprises an overlay of a patient's body, wherein the patient is positioned between said x-ray tube and said image receptor, wherein the patient's body is displayed concurrently with a skeleton frame comprising a plurality of pre-defined joints of the body, wherein said RGB camera captures a plurality of frames of the patient's body, wherein said display device is configured to alert a user when the patient moves by utilizing at least one of the following methods of coloring, blinking, flagging, generating audible sound, and displaying numerical scale for motion and said display device is configured to alert the user when a wrong body part of the patient is positioned between said x-ray tube and said image receptor by utilizing at least one of the following methods consisting of coloring, blinking, flagging, and generating audible sound, and wherein said display device is configured to alert the user when the body part is not centered by utilizing at least one of the following methods of coloring, blinking, flagging, and generating audible sound.

5. A system for improving quality in projection and tomographic x-ray imaging comprising:
an x-ray tube;
an image receptor;
a depth sensing device, wherein said image receptor is positioned to be aligned with said depth sensing device;
a RGB camera; and
a display device, wherein said display device is configured to display a depth-image view, collimated view, and skeleton view, wherein the depth-image view comprises a plurality of pixels, each of which represents a distance between said depth sensing device and each point of said image receptor that corresponds to each pixel, wherein the distance is measured by said depth sensing device, a collimated view comprises a targeted body part field and an image receptor field, the skeleton view comprises an overlay of a patient's body, wherein the patient is positioned between said x-ray tube and said image receptor, wherein the patient's body is displayed concurrently with a skeleton frame comprising a plurality of pre-defined joints of the body, wherein said RGB camera captures a plurality of frames of the patient's body, and wherein said display device is configured to adjust an alignment of the collimated radiation field according to the movement of the body part such that the body part remains motionless within the collimated radiation field.

* * * * *